(12) United States Patent
Moser et al.

(10) Patent No.: US 9,289,561 B2
(45) Date of Patent: Mar. 22, 2016

(54) REVERSELY ROTATABLE DOSE SETTING MECHANISM FOR AN INJECTION DEVICE

(75) Inventors: Ulrich Moser, Heimiswil (CH); Christian Schrul, Burgdorf (CH); Juerg Hirschel, Aarau (CH); Markus Tschirren, Kirchberg (CH)

(73) Assignee: TecPharma Licensing AG, Burgdorf (CH)

( * ) Notice: Subject to any disclaimer, the term of this patent is extended or adjusted under 35 U.S.C. 154(b) by 848 days.

(21) Appl. No.: 12/604,123

(22) Filed: Oct. 22, 2009

(65) Prior Publication Data

US 2010/0114037 A1    May 6, 2010

Related U.S. Application Data (63) Continuation of application No. PCT/CH2008/000180, filed on Apr. 22, 2008.

(30) Foreign Application Priority Data

Apr. 23, 2007   (DE) .......................... 10 2007 019 124

(51) Int. Cl.
  *A61M 5/00*    (2006.01)
  *A61M 5/315*   (2006.01)
  *A61M 5/20*    (2006.01)

(52) U.S. Cl.
  CPC .............. *A61M 5/31593* (2013.01); *A61M 5/20* (2013.01); *A61M 5/31551* (2013.01); *A61M 5/31583* (2013.01); *A61M 5/31535* (2013.01)

(58) Field of Classification Search
  CPC ......... A61M 5/20; A61M 5/178; A61M 5/00; A61M 5/31583; A61M 5/31576; A61M 5/31565; A61M 5/31533; A61M 5/31525; A61M 5/31501; A61M 5/31593; A61M 5/3159; A61M 5/31551; A61M 5/31535; A61M 5/315; A61M 5/3155; A61M 5/31536
  USPC .................. 604/207, 208, 210, 211, 136, 209
  See application file for complete search history.

(56) References Cited

U.S. PATENT DOCUMENTS

| | | | |
|---|---|---|---|
| 5,104,380 A | * | 4/1992 | Holman et al. ............... 604/117 |
| 5,298,023 A | | 3/1994 | Haber et al. |
| 5,383,865 A | * | 1/1995 | Michel .......................... 604/232 |

(Continued)

FOREIGN PATENT DOCUMENTS

| | | |
|---|---|---|
| DE | 202 09 051 U1 | 4/2003 |
| DE | 10 2005 001 159.4 | 7/2006 |
| DE | 10 2005 023 824 A1 | 12/2006 |
| EP | 0 295 075 | 12/1988 |
| EP | 0 828 527 B1 | 7/2002 |
| WO | 02/053214 A1 | 7/2002 |
| WO | 2004/078239 A1 | 9/2004 |
| WO | 2006/089734 | 8/2006 |

*Primary Examiner* — Bhisma Mehta
*Assistant Examiner* — Bradley G Thomas, Jr.
(74) *Attorney, Agent, or Firm* — Dorsey & Whitney LLP; Stuart R. Hemphill, Esq.

(57) ABSTRACT

A dosing mechanism for use with an injection device to adjust a dose to be discharged from the injection device, the dosing mechanism including an adjusting element which can be moved relative to the dosing mechanism and including a coupling element for being releaseably coupled to a threaded bar associated with the injection device such that the adjusting element can be moved relative to the bar in one direction while a relative movement in the opposite direction is prevented, the dosing mechanism further including a retaining element with an engaging element for preventing the bar from being rotated in at least one direction, and a releasing element for uncoupling the adjusting element and bar.

17 Claims, 4 Drawing Sheets

(56) References Cited

U.S. PATENT DOCUMENTS

| | | | | |
|---|---|---|---|---|
| 5,591,136 A | * | 1/1997 | Gabriel | 604/211 |
| 5,626,566 A | * | 5/1997 | Petersen et al. | 604/208 |
| 6,001,089 A | * | 12/1999 | Burroughs et al. | 604/506 |
| 6,193,698 B1 | * | 2/2001 | Kirchhofer et al. | 604/211 |
| 6,203,530 B1 | * | 3/2001 | Stewart, Sr. | 604/207 |
| 2004/0236285 A1 | | 11/2004 | Fisher et al. | |
| 2005/0065477 A1 | * | 3/2005 | Jost | 604/207 |
| 2007/0016142 A1 | * | 1/2007 | Burren et al. | 604/207 |
| 2008/0071227 A1 | * | 3/2008 | Moser et al. | 604/207 |
| 2008/0183139 A1 | | 7/2008 | Burren et al. | |
| 2009/0198193 A1 | * | 8/2009 | Veasey et al. | 604/207 |

\* cited by examiner

REVERSELY ROTATABLE DOSE SETTING MECHANISM FOR AN INJECTION DEVICE

CROSS-REFERENCE RELATED APPLICATIONS

This application is a continuation of International Patent Application No. PCT/CH2008/000180 filed Apr. 22, 2008, which claims priority to German Patent Application No. DE 10 2007 019 124.5 filed Apr. 23, 2007, the entire contents of both of which are incorporated herein by reference.

BACKGROUND

The present invention relates to devices for injecting, administering, infusing, delivering or dispensing a substance, and to methods of making and using such devices. More particularly, it relates to dose setting mechanisms for an injection device and, more particularly, to a dose setting mechanism by which a dose, amount or quantity of a substance to be dispensed from an injection device can be set or selected.

Document DE 202 09 051 U1 discloses an injection device with a dose setting element blocked or locked in an end position, which is able to effect a rotating movement relative to the housing in a first direction as far as an end position to select a product dose and in an opposite direction. The dose setting element is coupled with a conveying mechanism by which a selected product dose can be dispensed from a reservoir. An anti-rotation mechanism prevents a rotating movement of the dose setting element beyond an end position in the first direction of rotation.

Patent specification EP 0 828 527 B1 discloses an injection device with a longitudinally displaceable drive sleeve, a printed dose label to enable a reading to be taken of a dose to be injected, and a mechanism which prevents the injection device from being charged when the supply in an ampoule has been completely used. An actual possible dose which can be administered can be read from the dose setting mechanism on a dose scale provided in the region of a top end of the drive sleeve.

A dose setting mechanism for an injection device with a translation ratio is known from German patent application No. 10 2005 001 159.4. A small dose quantity can be exactly set and dispensed.

WO 2004/078239 A1 discloses a medicament administering device with a housing with an internal thread, a dose selection sleeve with a thread which locates in the internal thread of the housing, a rotating sleeve which is releasably connected to the dose selection sleeve and a coupling disposed between the dose selection sleeve and rotating sleeve. The two sleeves are able to rotate relative to the housing when coupled. When the dose selection sleeve and rotating sleeve are uncoupled, the dose selection sleeve can be rotated relative to the housing whereas the rotating sleeve is locked to prevent a rotation relative to the housing, thereby enabling an axial movement of the rotating sleeve so that a force is transmitted in the longitudinal direction to the proximal end of the medicament administering device.

DE 10 2005 023 824 A1 discloses a dose setting mechanism for setting a dose to be dispensed from an injection device, with a setting element including a setting sleeve and a priming element, a rotating sleeve which can be rotated out of the dose setting mechanism to prepare for dispensing a dose. A stop is provided on the setting element and a complementary stop is provided on the priming element so that a rotating movement of the priming element relative to the setting element can be restricted by the stops. A method of setting a dose to be dispensed from an injection device is also disclosed. The method includes setting a dose to be dispensed by using a setting element, e.g., a setting sleeve, and priming the injection device by using a priming element, e.g. a rotating sleeve, which, by a rotating movement, enables the set dose to be dispensed from the injection device in a subsequent step. The setting operation is uncoupled from the priming operation.

WO 02/053214 A1 discloses a dose setting mechanism for use in combination with a container filled with liquid. The dose setting mechanism is designed to permit a repeated injection of individually set liquid doses from the container. The dose setting mechanism comprises a housing, a drive element connected to the housing and designed to eject a liquid dose from the container, a spring element mounted in the housing, and a dose setting system mounted in the housing and connected to the spring element. The dose setting system comprises a dose setting element which can be moved in a first direction against the biasing force of the spring element to a selected setting position, the movement of the dose setting element being accompanied by a tensing of the spring; and a lock element connected to the housing and designed to retain the dose setting element in the set position against the biasing force of the spring element, wherein, when the lock element is triggered, the dose setting element drives the drive element to eject a set dose from a container filled with liquid, wherein the force for ejecting the set dose is transmitted by the spring element, and wherein the dose setting element is able to move in a second direction to enable the setting position to be selectively set.

SUMMARY

An object of the present invention is to provide a dose setting mechanism for setting and/or dispensing a dose to be dispensed from an injection device. Another object is to provide an injection device incorporating a dose setting mechanism. Another object is provide for the convenient and correctable setting of a dose to be dispensed from an injection device or the like.

In one embodiment, the present invention comprises a dosing mechanism for use with an injection device to adjust a dose to be discharged from the injection device, the dosing mechanism comprising a moveable adjusting element which can be moved relative to the dosing mechanism and comprising a coupling element for being releaseably coupled to a threaded bar associated with the injection device such that the adjusting element can be moved relative to the threaded bar in one direction while a relative movement in the opposite direction is prevented, the dosing mechanism further comprising a retaining element with an engaging element for preventing the threaded bar from being rotated in at least one direction, and a releasing element for uncoupling the adjusting element and threaded bar.

In one embodiment, the present invention relates to a dosing mechanism for an injection device to adjust a dose to be discharged from an injection device, the dosing mechanism comprising an adjusting element which can be moved relative to the dosing mechanism and is provided with a coupling element to be coupled to a threaded bar of the injection device in such a way that the adjusting element can be moved relative to the threaded bar in one direction while a relative movement in the opposite direction is prevented. In some embodiments, the dosing mechanism further comprises a retaining element fitted with an engaging element to prevent the threaded bar from being rotated in at least one direction. In some embodiments, the dosing mechanism comprises a releasing element which allows the coupling between the adjusting element and the threaded bar to be canceled.

In one embodiment, the present invention comprises a dose setting mechanism for an injection device for setting a dose (or amount or quantity) of a medicinal substance to be dispensed from the injection device. The substance, e.g. insulin, hormones, etc., may be contained in the injection device or in an ampoule inserted in or carried by the injection device. In some embodiments, the injection device comprises a threaded rod which can be rotated in and/or guided by an internal thread of the injection device to dispense a dose. For exemplary embodiments of such a threaded rod and an injection device of the type that may be used or incorporated in accordance with the present invention with embodiments of the dose setting mechanism in accordance with the present invention, reference may be made to DE 10 2005 023 824 A1, owned by the owner of the present application, the teachings of which, including the teachings relating to the threaded rod, dose setting and injection device, are incorporated herein by reference. (An English equivalent of DE 10 2005 023 824 is US Publication 2008/0183139 A1.) In some embodiments, retaining elements are provided on the threaded rod, which are able to secure the threaded rod to prevent it from turning in one or both directions. For example, the thread of the threaded rod may have teeth, such as is described in DE 10 2005 023 824. It is also possible to provide retaining elements on the threaded rod which do not lie against the external thread of the threaded rod, such as an annular or circumferentially extending toothed region. Such retaining elements retain the threaded rod in a position of rotation and lock it to prevent a rotation in at least one direction, and the threaded rod can advantageously be rotated in a direction opposite the retaining direction depending on the locating element locating in the retaining element or elements.

In some embodiments, a setting element, such as a rotating sleeve for example, is disposed alongside or on the threaded rod to enable the setting element to be moved relative to the threaded rod, e.g. rotated, so that the positional relationship between the setting element and threaded rod can be varied by a setting operation, as described in DE 10 2005 023 824 for example. In some preferred embodiments, the threaded rod is retained by a retaining element which is connected to the injection device or to a guiding sleeve which will be described below, thereby enabling the setting element, e.g. the rotating sleeve, to be rotated about the threaded rod to set the quantity on completion of the setting operation and trigger an injection of substance. Accordingly, the setting element can be rotated relative to the threaded rod and also pushed in the axial direction along the threaded rod, which can be achieved due to the fact that the setting element or rotating sleeve has an internal thread in which the external thread of the threaded rod locates. Alternatively, it is possible that the rotating sleeve is rotated relative to the threaded rod only, without being pushed in the axial direction.

In some preferred embodiments, the setting element or the rotating sleeve is coupled with a spring element, which can be tensed by rotating the setting element, for example, and which absorbs or stores the energy needed to dispense the substance. The stored energy is then transmitted from the setting element or rotating sleeve to the threaded rod when the threaded rod is released so that it moves in the distal direction of the injection device when the threaded rod is guided in an internal thread of the injection device to convert the rotating movement of the rotating sleeve into a forward translating movement of the threaded rod.

In some preferred embodiments, a retaining element of the injection device, such as a guiding sleeve, is fixedly connected to the injection device and forms part of the housing or is integrated in the housing of the injection device. In some embodiments, the retaining element comprises a retaining element such as a catch arm or snapper arm, for example, which locate in other retaining elements, such as teeth, a circumferentially extending ring or a toothed thread, of the threaded rod and prevent a rotating movement of the threaded rod. When the coupling between the retaining element and the threaded rod is released by pushing in a trigger, e.g. a button, the threaded rod, acted on by the spring force of the setting element primed during the setting movement, is driven with and rotated by the setting element to move the threaded rod in the distal (or forward or front) direction of the injection device and thus cause the substance to be dispensed.

In some preferred embodiments, the coupling of the locating element or elements of the setting elements in the threaded rod is designed so that the setting element can be moved in only one direction relative to the threaded rod and, in some preferred embodiments, in only one direction of rotation, whereas a movement or rotation of the setting element in the opposite direction is prevented by the locating elements of the setting element locating in the retaining element or elements of the threaded rod. The setting element is therefore coupled with the threaded rod to prevent it rotating relative to a locking direction, whereas the setting element is able to rotate relative to the threaded rod in the opposite direction, a direction of rotation or releasing direction. This coupling may be achieved using the teeth of the threaded rod and/or a locating element, for example, which has a flat and a steep flank.

In some embodiments of the present invention, the coupling between the rotating sleeve and threaded rod can be released during a setting operation, for example to enable a dose to be corrected by rotating the rotating sleeve back if too high a dose was set. A displaceable or rotatable dose correcting element which releases the coupling between the setting element and threaded rod may be provided for this purpose. For example, a dose correcting element, in some embodiments having an inclined surface, which can be moved parallel with the threaded rod may be provided. When pushed into the region of the coupling between the setting element and threaded rod, the element releases the coupling of the setting element with the threaded rod via the inclined surface, for example by lifting or deflecting or pushing away the locating elements, which also have an inclined surface serving as a contact surface for the dose correcting element. Thus, the setting element is able to move freely relative to the threaded rod or can be freely rotated in each direction. When the releasing element has been pushed out, the setting element may be coupled with the threaded rod again in the corrected position or rotational position for correcting the dose.

Accordingly, in some embodiments of the present invention, a setting element or a rotating sleeve may be provided on the toothed/threaded rod which can be moved or turned in one direction to set a dose, and the rotating sleeve is automatically locked to prevent it from turning back. This friction-induced retention of the setting element or rotating sleeve may be released by lifting the element of the sleeve producing the frictional hold, in other words due to the fact that the engagement of the rotating sleeve in the teeth of the toothed threaded rod is released, thereby enabling the rotating sleeve to be turned back to correct the dose.

In some embodiments of the present invention, the releasing element for uncoupling the setting element from the threaded rod may also be part of the trigger mechanism, e.g. comprising a button, which has a releasing element extending between the setting element and threaded rod as far as the coupling, and enables the setting element to be uncoupled from the threaded rod when the trigger button is pushed in slightly. In some preferred embodiments, the releasing element is disposed so that the setting element can be released from the threaded rod but without causing triggering, in other words without the threaded rod being released by the retaining element holding the threaded rod.

In some embodiments, a dose setting mechanism in accordance with the present invention provides a way in which a dose can be corrected, for example as a threaded rod is guided in a setting element or in a rotating sleeve, and the quantity of substance to be dispensed is fixed by the setting element which, when in an initial position, permits a setting or rotating movement in one direction only, thereby resulting in a simplified design of the setting element. If too high a dose is set when setting the dose, it can be corrected after the setting element has been uncoupled from the threaded rod by the dose correcting element by turning the setting or dose setting element back, without any dispensing taking place at the same time.

In another embodiment of the present invention, the setting element or rotating sleeve is freely rotatable on a threaded rod or a toothed threaded rod during the setting operation and, in some preferred embodiments, no locating element, for example a snapper arm of the rotating sleeve, locates in the threaded rod, thereby permitting a free setting movement, e.g. a free forward and reverse rotating movement. The coupling between the rotating sleeve and threaded rod is not established until the dose has been fully set and optionally corrected. This may be achieved due to the fact that a retaining element or catch element is moved by a displaceable ring so that it locates in a co-operating complementary catch element of the rotating sleeve and threaded rod so that once the ring has been moved, a coupling can be established between the setting element and threaded rod, thereby preventing any rotation.

In some embodiments, an alternative to such an anti-rotation lock, the rotating sleeve may also be coupled with the threaded rod when the setting movement terminates so that a movement of the setting element or rotating sleeve relative to the threaded rod is possible in one direction only.

In some preferred embodiments, the coupling between the retaining element and threaded rod and/or between the setting element and threaded rod is operated by at least one locating element, for example a snapper arm biased radially inwardly. In some embodiments, the locating element is designed so that, in co-operation with appropriate complementary or retaining elements or teeth of the threaded rod, the threaded rod is either fully retained, in other words is rotationally locked to prevent a rotation in both directions, or is rotationally locked in only one direction, as is the case when the setting element and threaded rod are coupled, for example on the basis of a ratchet mechanism of a type known per se.

In some embodiments, a displaceable coupling element of the type mentioned above which can be moved in an axial direction of the threaded rod to establish a coupling between the setting element and threaded rod may be part of the setting element or part of a trigger mechanism, for example a trigger button, or may be a separate element, for example a sliding switch. If the user notices that the dose set by the setting element is too high, the displaceable coupling element can be pushed to release the coupling between the setting element and threaded rod. Another option is that the setting element is not coupled with the threaded rod at all during the setting operation and the coupling is not established until the setting operation has been completed and prior to initiating the triggering operation or injection.

In some embodiments, the present invention comprises an injection device comprising an embodiment of a dose setting mechanism of the type described above.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 1:
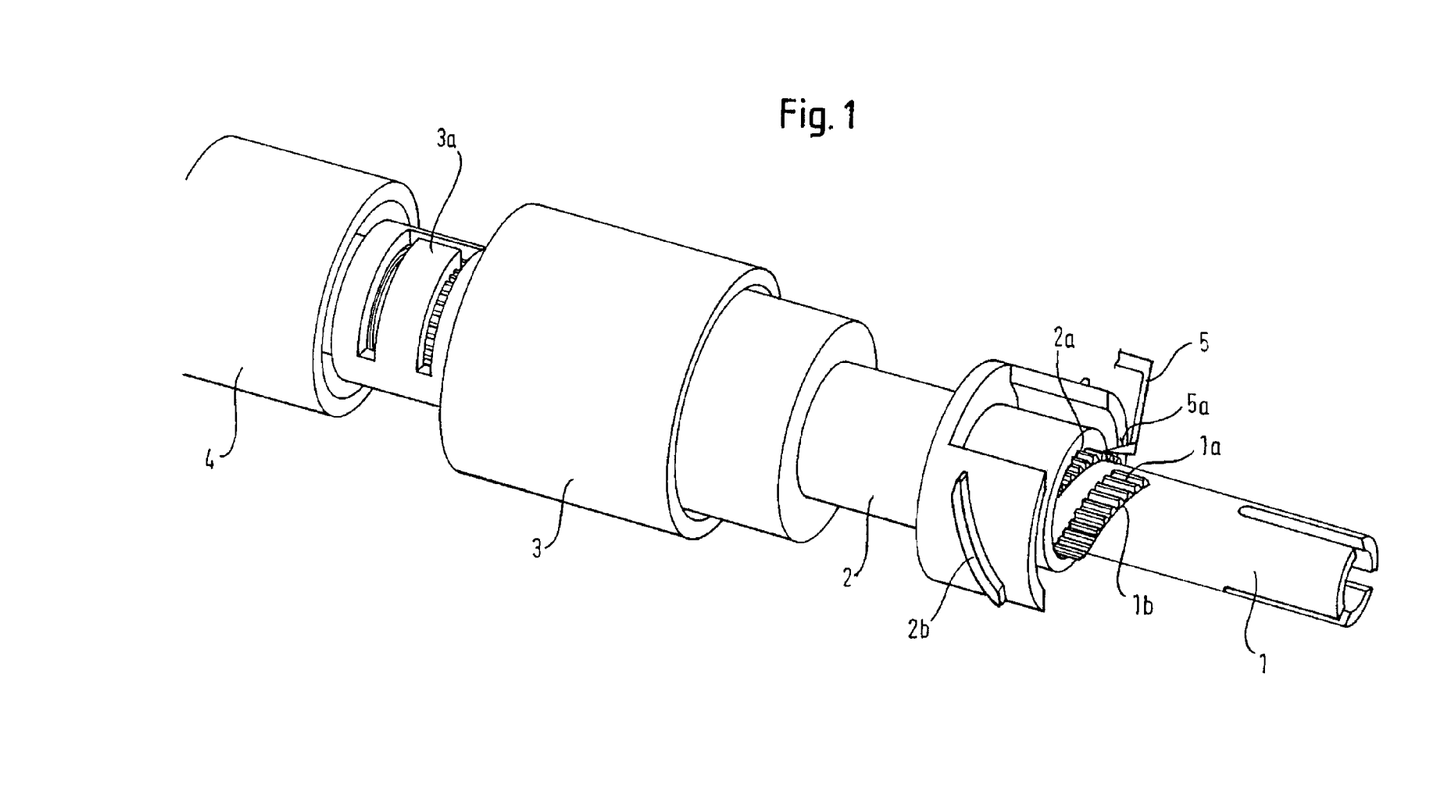
FIG. 1 is a perspective view of one embodiment of a dose setting mechanism in accordance with the present invention.
Figure 2:
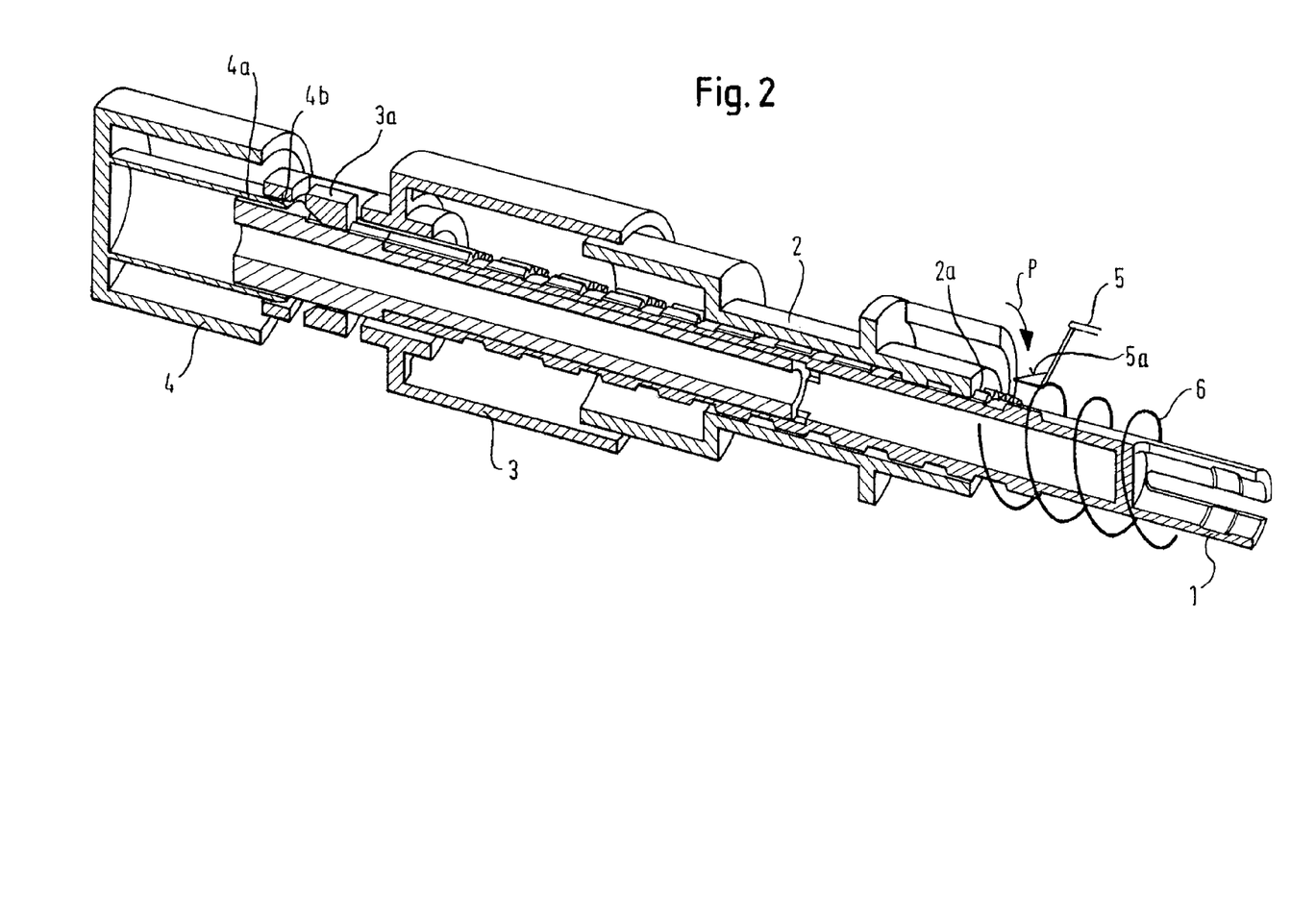
FIG. 2 is a cross-sectional view of the dose setting mechanism illustrated in FIG. 1.
Figures 3A, 3B:
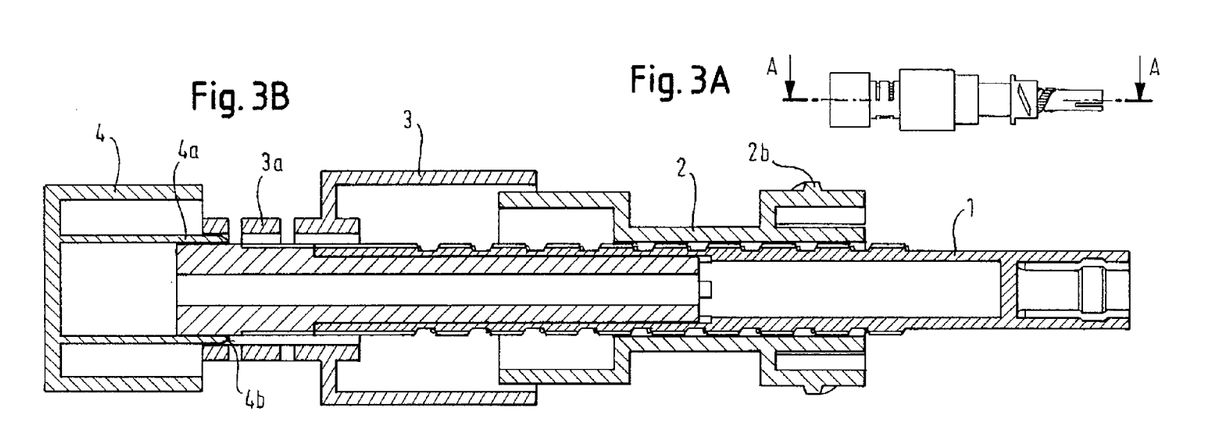
FIG. 3A is a plan view of the dose setting mechanism of FIG. 1.
FIG. 3B is a cross-sectional view along line A-A of FIG. 3A.
Figures 4A, 4B:
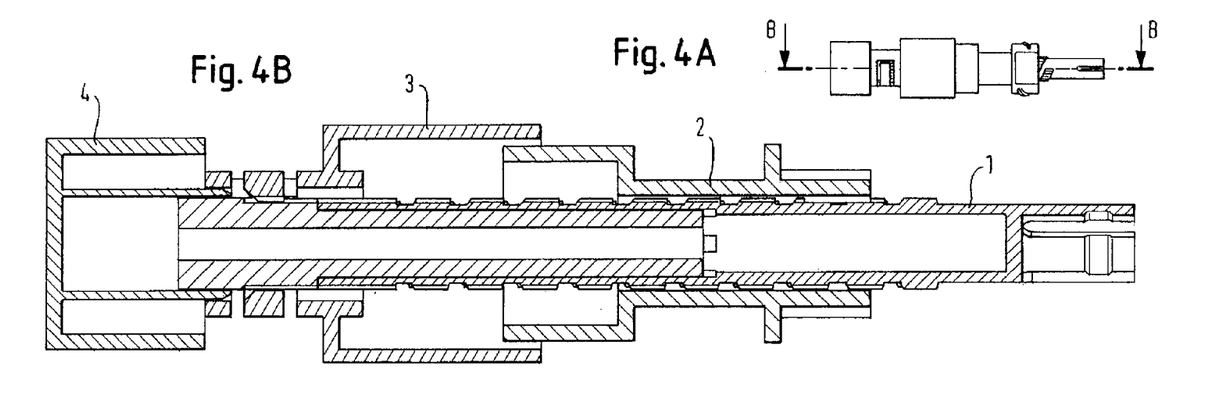
FIG. 4A is a plan view of the dose setting mechanism illustrated in FIG. 3A, rotated by 90°.
FIG. 4B is a cross-sectional view along line B-B indicated of FIG. 4A.

FIG. 1 illustrates a toothed-threaded rod 1 (which also may be referred to and/or thought of as a bar, plunger or the like) with a circumferentially extending thread 1b incorporating teeth 1a. Disposed around the threaded rod 1 is a rotating sleeve 2 serving as a setting element, which has locating elements 2a, as also illustrated in FIG. 2, which locate in the teeth 1a of the threaded rod 1 and permit a rotation of the rotating sleeve 2 relative to the threaded rod 1 in a direction indicated by arrow P in FIG. 2 and prevent a rotation in the opposite direction.

A guiding sleeve 3, which may be part of a housing of the injection device, is disposed around the threaded rod 1 and has or carries a snapper arm 3a which prevents a rotation of the threaded rod 1.

The external thread 1b of the threaded rod 1 is guided in an internal thread of the injection device, although this is not illustrated herein. (But see, for example, DE 10 2005 023 824 and/or its English equivalent US Publication 2008/0183139 A1, incorporated herein by reference).

If too high a dose is set by a rotation of the rotating sleeve 2 which, in the embodiment illustrated as an example, has an external thread 2b which can locate in a co-operating internal thread of the injection device, thereby enabling the rotating sleeve 2 to be displaced in the axial direction of the injection device during a setting operation, the rotating sleeve 2 can be uncoupled from the threaded 1 by a schematically illustrated releasing element 5. The releasing element 5 has an inclined surface 5a and can therefore be pushed between the rotating sleeve 2 and threaded rod 1 to release the engagement of the locating element 2a in the threaded rod 1, enabling the dose that has been set too high to be turned back and/or corrected. To this end, the rotating sleeve 2 may have a co-operating inclined surface on its front face, making it easier to push in the releasing element 5 and effect the release or uncoupling. The releasing element 5 may be provided in the form of an element which can be operated or moved from outside or alternatively, for example, by a displaceable sleeve.

To trigger an injection, the coupling between the guiding sleeve 3 serving as a retaining element and the rod 1 can be released by pushing in the trigger button 4 in the direction of the guiding sleeve 3. To this end, the trigger button 4 has releasing elements 4a projecting in the axial direction with inclined front faces 4b, which can be moved into contact with co-operating inclined complementary surfaces of the snapper arms 3a of the guiding sleeve 3 and lift the snapper arm or arms 3a, in other words move them radially outwardly away from the rod 1, as the trigger button 4 is pushed further in, thereby releasing the rotation lock or retention of the threaded rod 1.

No longer retained by the guiding sleeve 3, the threaded rod 1 is now driven by the rotating sleeve 2, which is turned back by the spring 6. The spring was tensed during the setting operation, but can now relax again, which causes a rotating movement of the threaded rod 1 and hence a movement of the threaded rod 1 in the distal direction of the injection device. The rotating and forward movement of the rod is provided and guided by the coupling between the thread 1b of the threaded rod 1 in an internal thread of the injection device. Thus, the set dose is dispensed.

Alternatively or in addition to releasing the coupling between the rotating sleeve 2 and rod 1, by virtue of another aspect of the present invention, the coupling between the rotating sleeve 2 and rod 1 is not established until a dose has been fully set and corrected if necessary. This is enabled by a catch element which is moved by a displaceable ring so that it locates with the rotating sleeve 2 and the teeth 1a of the rod 1.

Figure 5:
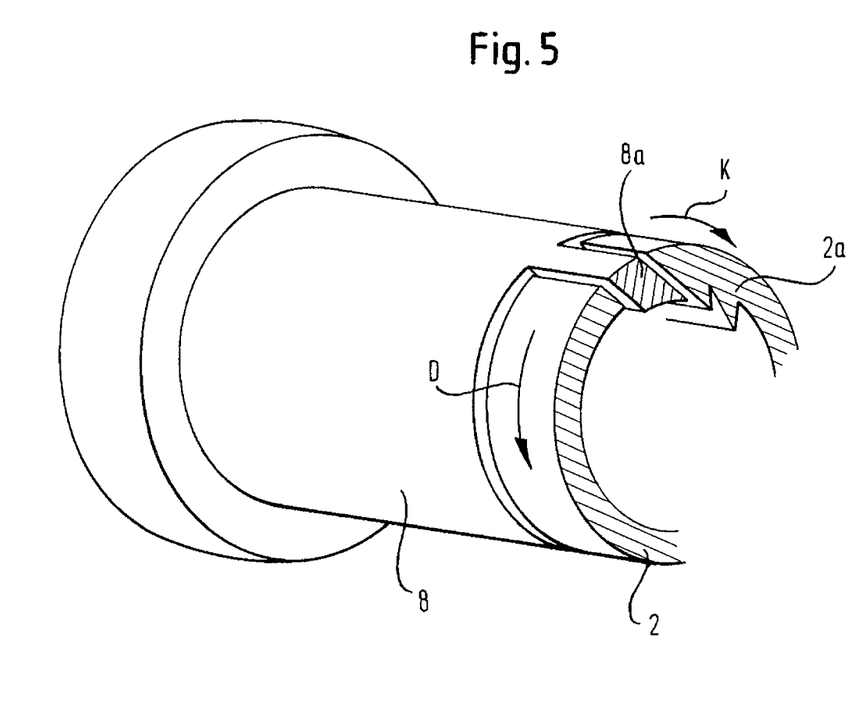
FIG. 5 is a perspective view of another embodiment of a dose correcting mechanism in accordance with the present invention.

FIG. 5 illustrates another embodiment in accordance with the present invention wherein the dose is set by a dose setting sleeve 8 with one or more snapper arm lifts or lifting means 8a, which locate in the rotating sleeve 2 or co-operate with the snapper arms 2a so that a rotation is transmitted in the dose setting direction (arrow D), and a rotation in the correcting direction (arrow K) causes the snapper arms 2a to be lifted due to the inclined surface of the snapper lifts or lifting means 8a. The snapper arms 2a are therefore uncoupled from the threaded rod 1.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A dose setting mechanism for an injection device for setting a dose to be dispensed from the injection device, comprising:
   a threaded rod associated with the injection device;
   a dose setting element comprising a rotating sleeve which can be rotated relative to the dose setting mechanism and which carries a coupling element permitting a coupling with the threaded rod so that the rotating sleeve can be rotated relative to the threaded rod in one, setting direction to set a dose and a relative rotation in an opposite direction is blocked;
   a retaining element fixedly connected to the injection device which carries a locating element; and
   a releasing element comprising an inclined surface,
   wherein the coupling between the coupling element of the dose setting element and the threaded rod can be uncoupled by the inclined surface such that rotation of the rotating sleeve relative to the threaded rod in said opposite direction is enabled and a set dose can be turned back or corrected, and
   wherein, during rotation of the rotating sleeve in the opposite direction, the locating element prevents movement of the threaded rod.

2. The dose setting mechanism as claimed in claim 1, wherein at least one of the locating element and the coupling element comprise an elastic region.

3. The dose setting mechanism as claimed in claim 1, wherein at least one of the locating element and the coupling element comprise a catch arm.

4. The dose setting mechanism as claimed in claim 1, further comprising a spring operably connected to the dose setting element, wherein the spring is tensed due to rotation of the rotating sleeve in the setting direction.

5. The dose setting mechanism as claimed in claim 1, wherein the threaded rod further comprises teeth.

6. The dose setting mechanism as claimed in claim 5, wherein the injection device further comprises a trigger element by which a coupling between the retaining element and the threaded rod can be released.

7. The dose setting mechanism as claimed in claim 6, in which the trigger element comprises an inclined surface relative to a radial plane.

8. The dose setting mechanism as claimed in claim 1, wherein the dose setting element comprises an external thread which is able to locate in an internal thread of the injection device.

9. The dose setting mechanism as claimed in claim 1, wherein the threaded rod comprises an external thread with teeth.

10. The dose setting mechanism as claimed in claim 1, wherein the threaded rod comprises a circumferentially extending region in which at least one of teeth and fixing elements are provided.

11. A dose setting mechanism for an injection device comprising:
   a rod;
   a dose setting element comprising a rotating sleeve for setting a dose;
   a coupling element for coupling the rod and the dose setting element, said coupling element flexibly joined to the dose setting element, wherein said coupling element engages with the rod and permits rotation of the rotating sleeve in a setting direction and blocks rotation of the rotating sleeve in an opposite direction;
   a retaining element fixedly connected to the injection device which carries a locating element;

a releasing element comprising an inclined surface for uncoupling the rod and dose setting element; and
a trigger element;
wherein actuation of the releasing element causes the inclined surface to flex the coupling element such that the rod is uncoupled from the dose setting element thereby enabling the rotating sleeve to rotate in the opposite direction to turn back or correct a set dose, and
wherein, during rotation of the rotating sleeve in the opposite direction, the locating element prevents movement of the rod.

12. The dose setting mechanism according to claim 11, wherein the retaining element carries an arm for flexibly engaging the locating element with the rod.

13. The dose setting mechanism according to claim 12, wherein the trigger element is for uncoupling the flexible engagement between the locating element and the rod.

14. A dose setting mechanism for an injection device for setting a dose to be dispensed from the injection device, comprising:
a threaded rod;
a dose setting element comprising a sleeve and a coupling element joined to the sleeve, wherein the sleeve is rotatable about the threaded rod in a first direction in a dose setting movement and a relative movement of the sleeve in an opposite direction is blocked by an engagement between the coupling element and the threaded rod;
a retaining element fixedly connected to the injection device; and
a releasing element comprising an inclined surface movably engagable with the coupling element of the dose setting element,
wherein an engagement of the inclined surface with the coupling element causes the coupling element to move out of the engagement with the threaded rod such that the relative movement of the sleeve in the opposite direction in a dose correcting or turning back movement is permitted, and
wherein the retaining element is in an engagement with the threaded rod and prevents movement of the threaded rod during rotation of the sleeve in the opposite direction.

15. The dose setting mechanism according to claim 14, wherein the retaining element comprises a locating element configured to engage with the threaded rod to block the rotating movement of the threaded rod.

16. The dose setting mechanism according to claim 15, further comprising a trigger element by which the engagement between the retaining element and the threaded rod can be released.

17. The dose setting mechanism according to claim 16, further comprising a spring operably connected to the dose setting element, wherein the spring is tensed by a setting movement of the dose setting element, and upon actuating the trigger element, the engagement between the retaining element and the threaded rod is released and the tensed spring relaxes thereby causing the dose setting element and the threaded rod to rotate in a dose dispensing movement.

\* \* \* \* \*